United States Patent
Weber et al.

(10) Patent No.: US 10,292,814 B2
(45) Date of Patent: May 21, 2019

(54) BIOLOGICAL HEART VALVE REPLACEMENT, PARTICULARLY FOR PEDIATRIC PATIENTS, AND MANUFACTURING METHOD

(71) Applicant: Universitaet Zuerich, Zurich (CH)

(72) Inventors: Benedikt Weber, Zurich (CH); Simon Philipp Hoerstrup, Zurich (CH)

(73) Assignee: Universitaet Zuerich, Zurich (CH)

( * ) Notice: Subject to any disclaimer, the term of this patent is extended or adjusted under 35 U.S.C. 154(b) by 0 days.

(21) Appl. No.: 15/023,006

(22) PCT Filed: Sep. 24, 2014

(86) PCT No.: PCT/EP2014/070355
§ 371 (c)(1),
(2) Date: Mar. 18, 2016

(87) PCT Pub. No.: WO2015/044193
PCT Pub. Date: Apr. 2, 2015

(65) Prior Publication Data
US 2016/0220361 A1  Aug. 4, 2016

(30) Foreign Application Priority Data
Sep. 25, 2013 (EP) .................................. 13186027

(51) Int. Cl.
*A61F 2/24* (2006.01)
*A61L 27/18* (2006.01)
*A61L 27/48* (2006.01)

(52) U.S. Cl.
CPC .......... *A61F 2/2412* (2013.01); *A61F 2/2415* (2013.01); *A61L 27/18* (2013.01);
(Continued)

(58) Field of Classification Search
CPC ...... A61F 2/07–2002/077; A61F 2/24–2/2475; A61F 2002/30706;
(Continued)

(56) References Cited

U.S. PATENT DOCUMENTS

| 5,383,926 A | 1/1995 | Lock et al. |
| 2003/0065386 A1 | 4/2003 | Weadock |

(Continued)

FOREIGN PATENT DOCUMENTS

| WO | 2009108355 A1 | 9/2009 |
| WO | 2012018779 A2 | 2/2012 |

OTHER PUBLICATIONS

Schoen FJ. Evolving concepts of cardiac valve dynamics: the continuum of development, functional structure, pathobiology, and tissue engineering. Circulation. Oct. 28, 2008;118(18):1864-80.

(Continued)

*Primary Examiner* — Yashita Sharma
*Assistant Examiner* — Rebecca S Preston
(74) *Attorney, Agent, or Firm* — Agris & Von Natzmer, LLP; Joyce Von Natzmer

(57) ABSTRACT

A biological heart valve replacement, particularly for pediatric patients, comprises a tubular segment (A) comprising a proximal end (Ep), a distal end (Ed) and a central portion (Pc) arranged between said proximal and distal ends and defining a longitudinal direction of the valve. The valve further comprises at least one inner leaflet (C) attached in hinge-like manner to a connection zone (F) at an inner wall (W) region of said central portion, each one of said inner leaflets being movable between a closing position and an opening position of the valve. In order to provide growth adaptability, the tubular segment comprises at least one tubular growth zone (B; B1,B2) configured as a longitudinal strip made of a growth-adaptive biomaterial, with the (Continued)

remainder of the tubular segment being made of a non-growth-adaptive biomaterial.

16 Claims, 1 Drawing Sheet

(52) U.S. Cl.
CPC ....... *A61L 27/48* (2013.01); *A61F 2210/0004* (2013.01); *A61F 2210/0057* (2013.01); *A61F 2230/0006* (2013.01); *A61F 2230/0023* (2013.01); *A61F 2250/001* (2013.01); *A61F 2250/0003* (2013.01); *A61F 2250/0014* (2013.01); *A61F 2250/0031* (2013.01); *A61F 2250/0051* (2013.01); *A61F 2250/0059* (2013.01); *A61F 2250/0082* (2013.01); *A61L 2430/20* (2013.01)

(58) Field of Classification Search
CPC ...... A61F 2250/0082; A61F 2250/0031; A61F 2250/0051
See application file for complete search history.

(56) References Cited

U.S. PATENT DOCUMENTS

| | | | |
|---|---|---|---|
| 2005/0228486 A1* | 10/2005 | Case | A61F 2/07 623/1.24 |
| 2006/0253188 A1 | 11/2006 | Case | |
| 2011/0066237 A1 | 3/2011 | Matheny | |
| 2013/0030521 A1 | 1/2013 | Nitzan et al. | |

OTHER PUBLICATIONS

Talwar S, Malankar D, Garg S, Choudhary SK, Saxena A, Velayoudham D, Kumar AS. Aortic valve replacement with biological substitutes in children. Asian Cardiovasc Thorac Ann. Oct. 2012;20(5):518-24.
Mirensky TL, Nelson GN, Brennan MP, Roh JD, Hibino N, Yi T, Shinoka T, Breuer CK. Tissue-engineered arterial grafts: long-term results after implantation in a small animal model. J Pediatr Surg. Jun. 2009;44(6):1127-32.
Hoerstrup SP, Cummings Mrcs I, Lachat M, Schoen FJ, Jenni R, Leschka S, Neuenschwander S, Schmidt D, Mol A, Günter C, Gossi M, Genoni M, Zund G. Functional growth in tissue-engineered living, vascular grafts: follow-up at 100 weeks in a large animal model. Circulation. Jul. 4, 2006;114(1 Suppl):I159-66.
Dolgin E. Taking tissue engineering to heart. Nat Med. 2011;17(9):1032-5.
Vogel G. Tissue engineering. Mending the youngest hearts. Science. 2011;333(6046):1088-9.
Hibino N, McGillicuddy E, Matsumura G, Ichihara Y, Naito Y, Breuer C, Shinoka T.Late-term results of tissue-engineered vascular grafts in humans. J Thorac Cardiovasc Surg. Feb. 2010;139(2):431-6.
Weber B, Scherman J, Emmert MY, Gruenenfelder J, Verbeek R, Bracher M. Injectable living marrow stromal cell-based autologous tissue engineered heart valves: first experiences with a one-step intervention in primates. Eur Heart J. 2011;32(22):2830-40.
Schmidt D, Dijkman PE, Driessen-Mol A, Stenger R, Mariani C, Puolakka A. Minimally-invasive implantation of living tissue engineered heart valves: a comprehensive approach from autologous vascular cells to stem cells. J Am Coll Cardiol. 2010;3;56(6):510-20.
Dijkman PE, Driessen-Mol A, Frese L, Hoerstrup SP, Baaijens FP. Decellularized homologous tissue-engineered heart valves as off-the-shelf alternatives to xeno- and homografts. Biomaterials. Jun. 2012;33(18):4545-54.
Weber B, Dijkman PE, Scherman J, Sanders B, Emmert MY, Grünenfelder J, Verbeek R, Bracher M, Black M, Franz T, Kortsmit J, Modregger P, Peter S, Stampanoni M, Roberta J, Kehl D, van Doeselaar M, Schweiger M, Brokopp CE, Wälchli T, Falk V, Zilla P, Driessen-Mol A, Baaijens FPT, Hoerstrup SP. Off-the-shelf human decellularized tissue-engineered heart valves in a non-human primate model. Biomaterials 2013, 34, 7269-80.
Brennan et al., Tissue engineered vascular grafts demonstrate evidence of growth and development when implanted in a juvenile animal model, Ann Surg. 2008, 248, 370-377.

* cited by examiner

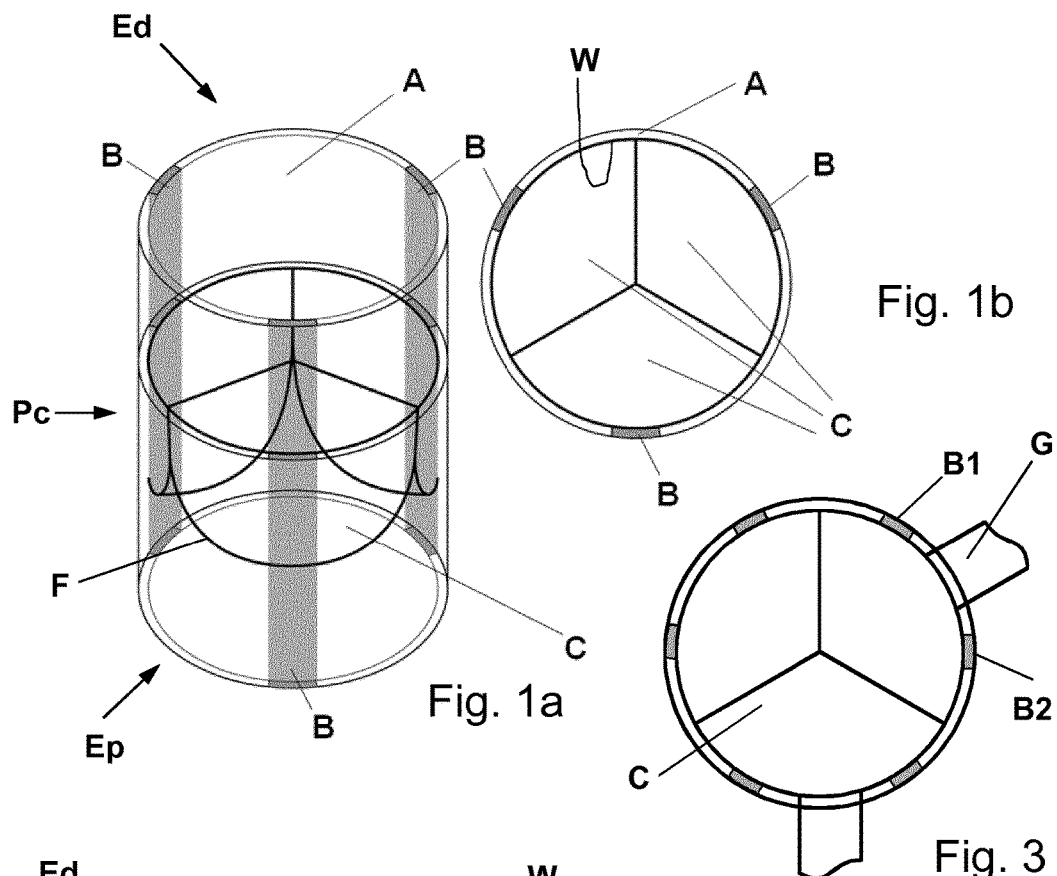
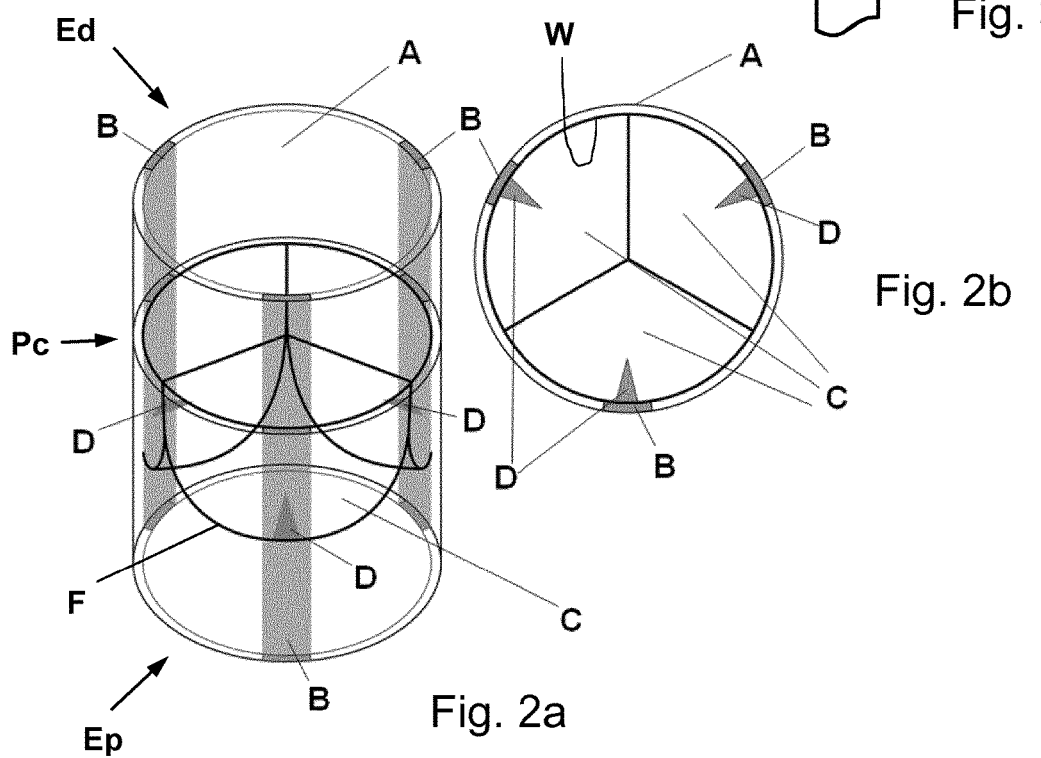

BIOLOGICAL HEART VALVE REPLACEMENT, PARTICULARLY FOR PEDIATRIC PATIENTS, AND MANUFACTURING METHOD

CROSS-REFERENCE TO RELATED APPLICATIONS

This is the U.S. national stage of International application PCT/EP2014/070355, filed Sep. 24, 2014 designating the United States and claiming priority to European application EP 13186027.2, filed Sep. 25, 2013.

FIELD OF THE INVENTION

The present invention generally relates to a biological heart valve replacement, particularly for pediatric patients. Moreover, the invention relates to a method of manufacturing a biological heart valve replacement, particularly for pediatric patients.

BACKGROUND OF THE INVENTION

Heart valve disease represents a major cardiovascular disease worldwide. Besides acquired heart disease, also congenital heart disease (affecting 1% of all life births) is responsible for a major disease global load. Currently used heart valve replacement constructs are fabricated from either metallic or fixed "biological" materials. The metal-based "mechanoprostheses" are prone to thromboembolic complications and lack growth-adaptive capacities (Schoen, 2008). While bioprosthetic materials, e.g. fabricated from glutaraldehyde-"fixed" xenogenic or homogenic native tissues, are not associated with an increased risk of clotting activation, they are still limited by the lack of growth-adaptive capacities of these implants. Particularly in pediatric patients this is of major concern, as the valvular annulus undergoes rapid changes throughout the physiological development and growth of the young patients. This implies that these young patients currently have to undergo repeated reoperations causing increased morbidity and mortality (Talwar et al., 2012). This aspect of growth has been addressed by a plethora of studies and investigations throughout the last 20 years. In particular, the field of cardiovascular tissue engineering has shown gradual success also demonstrating "growth-adaptation" in studies by independent groups focusing on tissue engineered arteries (Hoerstrup et al., 2006; Brennan et al., 2008).

However, while for tissue engineered arteries adequate function (and growth adaptation) could be demonstrated and the technology has also entered first-in-man clinical trials in Japan (Hibino et al., 2010) and the US (Vogel et al., 2011; Dolgin et al., 2011), the development of tissue engineered heart valves is experiencing obstacles partly derived from the complexity of the physiological environment of heart valves (Weber et al., 2011; Schmidt et al., 2010).

In particular, the radial leaflet shortening observed in ovine and non-human primate preclinical animal models is of major concern (Weber et al., 2011; Schmidt et al., 2010). Therefore, so far no tissue engineered heart valve has entered routine clinical practice, and therapy for patients with heart valve disease remains to be highly limited. However, a growth-adaptive heart valve replacement is of very high interest as the bioengineered valves would meet an even much higher medical need than in the case of vascular grafts (Vogel et al., 2011; Dolgin et al., 2011).

WO 2009/108355 A1 discloses a bioprosthetic heart valve replacement comprising a tubular segment that has a longitudinal strip of material forming a loop created by two releasable seams. When it becomes necessary to increase the lumen, the seams are broken or irreversibly deformed by the application of a radial force, such as by a balloon expandable member. US 2003/065386 A1 describes a radially expandable endoprothesis device which is constituted of a combination of superelastic alloys and bioresorbable materials. Another radially expandable heart valve is disclosed in WO 2012/018779 A2; it is based on a frame with rigid support elements that are slidingly connected to each other and thereby allow for an increase in diameter.

U.S. Pat. No. 5,383,926 A describes a re-expandable endoprothesis device formed by an elongated sleeve member having a longitudinal lateral slot, the edges of which are initially connected by expansion limiting means formed as strips disposed across the lateral slot. The device can be brought—by means of a balloon catheter—from an non-expanded configuration to a first expanded configuration, the latter being defined by the expansion limiting strips. By breaking or removing the strips, the device can be expanded further to a second expanded configuration, which is basically not limited by any restraining means. Only two specific embodiments of this second expansion step are described: breaking of the strips by reinsertion of the ballon catheter, or biodegration of the strips, in which case the sleeve needs to provide an inherent spring action driving the sleeve walls in radially outward direction.

US 2013/030521 A1 discloses a device for regulating blood pressure between a patient's left atrium and right atrium and comprising an hourglass-shaped stent region. In some embodiments the device includes one or more biodegradable components that increase the cross-sectional area of the device so as to compensate for tissue ingrowth. This is achieved in two possible ways: either by having a layer of biodegradable substance on the inner surface. Alternatively, a small-diameter constriction may be initially provided by sewing with a biodegradable thread, dissolution of which will lead to an opening up of the constriction.

US 2006/253188 A1 and US 2011/066237 A1 disclose prosthetic tissue valves which, in an unstressed position, are substantially planar and flat. They are generally configured to have a larger diameter than the inner diameter of an annulus in a defective valve to be replaced. For implantation the valve is brought into a folded, biased configuration that exerts a pressure in radially outward direction.

Accordingly, it is an object of the present invention to provide an improved biological heart valve replacement for pediatric patients that does not have the above mentioned shortcomings. In particular, the biological heart valve replacement of the present invention does not need insertion of a balloon catheter for being expanded, nor does it need to be provided with an inherent elastic force directed in radially outward direction. Another object of the present invention is to provide a method of manufacturing a biological heart valve replacement according to the invention.

SUMMARY OF THE INVENTION

The above and other objects are met by the biological heart valve replacement according to claim 1 and by the method according to claim 14.

Advantageous embodiments of the invention are defined in the dependent claims and/or are described hereinbelow.

According to one aspect of the invention, a biological heart valve replacement for pediatric patients comprises a tubular segment comprising a proximal end, a distal end and a central portion arranged between said proximal and distal ends and defining a longitudinal direction of the valve replacement. The valve replacement further comprises at least one inner leaflet attached in hinge-like manner to a connection zone at an inner wall region of said central portion, each one of said inner leaflets being movable between a closing position and an opening position of the valve. The tubular segment comprises at least one tubular growth zone configured as a longitudinal strip made of a growth-adaptive biomaterial, with the remainder of the tubular segment being made of a non-growth-adaptive biomaterial.

Throughout the present text, the term "heart valve replacement" shall be understood as an object, i.e. in the sense of a heart valve prosthesis, and not as an activity in the sense of a surgical intervention.

The term "biological heart valve replacement" shall be understood here as a heart valve replacement substantially made of a biomaterial.

The term "biomaterial" shall be understood here in accordance with the IUPAC definition, i.e. as a "material exploited in contact with living tissues, organisms or microorganisms".

The term "growth-adaptive biomaterial" shall be understood here as a biomaterial capable of increasing its size concomitantly with surrounding organ structures of a host. In contrast thereto, a "non-growth-adaptive biomaterial" shall be understood here as a biomaterial without substantial growth capability, such as e.g. a glutaraldehyde-fixed xerogenic or homogenic tissue.

The term "longitudinal strip" shall be understood in a broad sense, i.e. as also including generally elongated shapes with branchings or bifurcations, e.g. in order to avoid certain anatomic structures.

The present invention overcomes the disadvantages of currently known biological heart valve replacements by having integrated tubular growth zones, which provide the capacity of gradual radial expansion according to the physiological growth of children. The invention thus combines the advantages of clinically used biological (homologous or xenogenic) prostheses, which are not plagued by surface thrombogenicity but do not have growth-adaptive properties, and of certain non-biological heart valve prostheses designed to allow size adaptation but having the disadvantage of substantial thrombogenicity.

By virtue of the potential to adapt to the somatic growth of pediatric patients, the biological heart valve replacements according to the present invention are particularly useful for pediatric patients, as they will allow avoiding or at least reducing the number of reoperations that currently have to be performed in pediatric patients with a heart valve replacement. Therefore, the present invention may significantly reduce the morbidity and/or mortality in this group of patients.

The tubular growth zones may be integrated into i) conventional (surgical) biological bio-prostheses or ii) they may be used for a minimally invasive implantation approach. For the latter, the valves have to be integrated into a stent system, which holds the capacity of gradual radial expansion such as a) expandable stent systems, b) breakable stent systems or c) biodegradable stent systems). In the case of a) and b) the stent systems have to be expanded interventionally using balloon dilation of the stent in situ.

It will be understood that the size, number and location of tubular growth zones will depend on the particular valve design and application and should be selected so as to optimize expandability and ease of manufacturing. According to an advantageous embodiment (claim 2), the valve has one tubular growth zone for each inner leaflet, each growth zone traversing the connection zone of the respective inner leaflet.

Particularly for aortic valve replacements it may be preferable to have two circumferentially spaced apart tubular growth zones for each inner leaflet (claim 3). Such a paracoronary arrangement contributes to avoid any disruptive effects on coronary perfusion.

In principle the tubular growth zones could make up for a majority of the tubular context. According to an advantageous embodiment (claim 4), the entirety of the tubular growth zones forms an area that represents about 5 to about 50, preferably about 10 to about 30 area-% of the tubular segment. In the present context, "area-%" shall be understood as the percentage fraction of the growth zones area in relation of the total area of the tubular segment's outer surface.

While the tubular growth zones according to the present invention generally allow for adequate radial adaptation of the biological heart valve replacement, an additional problem in growing patients is caused by the need for a concomitant increase in inner leaflet size. Therefore, according to a particularly advantageous embodiment (claim 5), each inner leaflet further comprises a leaflet growth zone configured as a patch made of a growth-adaptive biomaterial and arranged in a leaflet region adjacent the connection zone where the leaflet is attached to the tubular segment in hinge-like manner.

This embodiment improves the "growth" adaptation of the entire heart valve complex and supports the maintenance of a physiological geometry of the heart valve. This should be of importance in the case of substantial radial expansion as—in spite of the expansion of the wall—the leaflet remains to be static due to the native tissue component. Therefore, the insertion of these additional zones introduces an expandable "strip" into the inner leaflets and thereby also allows for the circumferential adaptation of the leaflet belly.

According to one embodiment (claim 6), each leaflet growth zone is substantially triangular, with a triangle base adjacent the inner wall region and a triangular apex oriented radially inwards from the inner wall region. With a direct connection to the wall growth zone, this "growth triangle" allows for gradual circumferential length increase of the leaflet in the (non-coaptive) valve belly area (close to the hinge region) and allows for a more ideal growth-like expansion. This should be beneficial as it would i) allow for more extensive growth-adaptations and ii) prevent an inconsistency of the expanding ("growing") wall and the nonexpanding static leaflet by giving also the leaflet a dynamic (expansive) component.

Preferably (claim 7), the leaflet growth zone represents about 5 to about 50, particularly about 10 to about 30 area-% of the respective inner leaflet.

In one embodiment (claim 8) of the biological heart valve replacement, the non-growth-adaptive biomaterial is a fixed xenogenic tissue or a homogenic native tissue. As will generally be known to the skilled person, the term "fixed" use in relation with implantable tissue refers to biological tissue that has been treated with a fixation agent such as glutaraldehyde so as to preserve its mechanical properties in view of the intended use. In general, such fixed tissue will not have any substantial growth-adaptive properties, but has otherwise excellent properties regarding structural stability and wear resistance.

In contrast to the above, the tubular and leaflet growth zones are composed of biocompatible materials having growth-adaptive properties.

The material of these "growth zones" may be composed of either of i) a rapidly (bio-)degradable polymer, ii) animal derived (fixed or decellularized) tissues with expansive capacities or iii) (viable or decellularized) tissue engineered materials.

According to a first embodiment (claim 9), the growth-adaptive biomaterial is a biodegradable polymer that is gradually degraded and replaced by native tissue in vivo.

In an advantageous embodiment (claim 10), the biodegradable polymer is made from a polyglycolic acid (PGA) matrix dip-coated with poly-4-hydroxybutyrate (P4HB).

It is contemplated that the growth-adaptive biomaterial may be a native biological tissue with enhanced expansive properties.

According to yet another embodiment (claim 11), the growth-adaptive biomaterial is a tissue engineered material. Examples for such materials are in vitro engineered human cell-derived cellularized or decellularized matrices.

A further advantage of the proposed growth zones could be that they may serve as entrance point for autologous host cells repopulating the tissues and could ultimately also improve the recellularization of the non-viable bioprosthetic implant tissues.

It will be understood that the biological heart valve replacement will be configured in accordance with the intended use, i.e. the type of valve to be replaced, the age of the patients and any other physiological and surgical requirements. In general, the tubular segment could have a diameter of about 4 to about 50 mm and a length of about 5 to about 50 mm, with the smallest sizes to be used e.g. for fetal valve replacements or venous valve replacements and the largest sizes to be used e.g. in veterinary medicine. In a typical application for pediatric patients, the tubular segment has a diameter of about 5 to about 20 mm (claim 12) and a length of about 10 to about 20 mm (claim 13).

According to a further aspect of the invention, a method of manufacturing a biological heart valve replacement as defined above comprises the steps of:
a) providing a biological heart valve replacement comprising a tubular segment made of a non-growth-adaptive biomaterial, said tubular segment having a segment length and comprising a proximal end, a distal end and a central portion arranged between said proximal and distal ends and defining a longitudinal direction of the valve, the valve further comprising at least one inner leaflet attached to an inner wall region of said central portion, each one of said leaflets being configured to be movable between a closing position and an opening position of the valve;
b) applying at least one longitudinal cut along said tubular segment, thereby forming a pair of longitudinally aligned tube wall edges;
c) arranging a strip shaped piece of a growth-adaptive biomaterial having a length corresponding to said segment length and having longitudinal strip edges so as to be positioned between said pair of tube wall edges;
d) fixing each longitudinal strip edge to an adjacent tube wall edge.

As will be understood, the above method starts out with a biological heart valve replacement having a size that matches the present size requirements of a pediatric patient. The manufacturing method then comprises the insertion of an appropriate number of tubular growth zones. This is done by applying a longitudinal cut to the tubular segment and inserting an appropriately dimensioned strip of a growth adaptive material, followed by fixing the strip to the edges formed by the preceding cut.

According to one embodiment (claim 15), the fixing step d) is carried out by suturing or by gluing, e.g. with fibrin glue.

It will be understood that in order to manufacture a biological heart valve replacement further comprising leaflet growth zones, it will be advantageous to attach the latter directly to a corresponding strip-like tubular growth zone. When applying the longitudinal cut to the tubular segment, one will also make an appropriate incision into the adjacent valve leaflet. Such incision will be configured so as to leave free a valve leaflet portion corresponding to the leaflet growth zone to be inserted.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein are shown:

FIG. 1: a heart valve according to a first embodiment, (a) in a perspective schematic view, and (b) in a top view;

FIG. 2: a heart valve according to a second embodiment, (a) in a perspective schematic view, and (b) in a top view; and FIG. 3: a heart valve according to a third embodiment, in a top view;

DETAILED DESCRIPTION OF THE INVENTION

In the following, exemplary heart valve replacements are illustrated as a three-leaflet or tricuspid valves. However, it will be appreciated by the skilled person that such valve replacements may be configured to have just two leaflets or a larger number of leaflets depending on the intended application.

The biological heart valve replacement shown in FIGS. 1a and 1b comprises a tubular segment A having a proximal end Ep, a distal end Ed and a central portion Pc arranged between said proximal and distal ends and defining a longitudinal direction of the valve. The valve further comprises three inner leaflets C attached in hinge-like manner to respective connection zones F at an inner wall W region of the central portion. The inner leaflets are movable between a closing position as shown in FIGS. 1a and 1b and an opening position (not shown here) of the valve where the inner leaflets are flipped towards the valve's inner wall. The tubular segment comprises three tubular growth zones B configured as substantially rectangular longitudinal strips made of a growth-adaptive biomaterial. In the arrangement shown, each one of the three growth zones traverses the connection zone F of a respective inner leaflet. The remainder of the tubular segment is made of a non-growth-adaptive biomaterial.

In the biological heart valve replacement shown in FIGS. 2a and 2b, each inner leaflet C further comprises a triangle-shaped leaflet growth zone D which is directly connected to the main tubular growth zone B on the wall. In the arrangement shown here, the leaflet growth zones are arranged in a region around the bisecting axis of the respective leaflet.

FIG. 3 shows a further biological heart valve replacement which is particularly suited for aortic valve replacements. In this arrangement the tubular segment has a pair of tubular growth zones B1 and B2 for each one of the inner leaflets C. The two tubular growth zones B1 and B2 of each pair are arranged at opposite sides of the bisecting axis of the respective leaflet. As may be seen from the figure, the pair of growth zones B1 and B2 avoids overlapping with the angular position of a respective coronary artery G branching off from the aorta. It will be understood that this type of set-up requires appropriate angular orientation of the aortic valve replacement within the aorta. It will also be appreciated that each inner leaflet C may further comprise at least one leaflet growth zone. In this case, it would be appropriate to actually have a pair of triangle-shaped leaflet growth zones, each one being attached to an associated growth zone B1 or B2.

In manufacturing the biological heart valve replacement, the tubular growth zone-insert is integrated into the wall (or conduit) of the biological heart valve replacement by opening the wall area with a straight cut and inserting the growth material. The connection between the growth material and the wall can be achieved either i) mechanically by sutures or ii) chemically by glue-based connection (i.e. using fibrin glue). The size of the insert is flexible and depends on the needs of the individual patient (pediatric or adult patient) and the type of replacement construct (surgical versus catheter)—implying that different sizes of the valves and inserts could be provided for treatment. With the size of the insert one can also determine the radial growth/expansion capacity. In principle, there is no limit other than the natural borders formed by the leaflet commissures. However, in the case of a "normal" heart valve of an adult (with an annulus size of 25 mm and a replacement size of 29 mm diameter) the dimensions of the growth zone calculated with 25%-33% of the total inner annular diameter should be sufficient for the circumferential growth zone length. The longitudinal length is limited by the implant (natural ending in case of surgical implants; stent ending in case of transcatheter implants). The biological valves used for these bio-prostheses will need a profound oversizing of the leaflets to ensure valvular co-aptation after growth-adaptation/expansion.

For integration into the "growth zones" several different (bio-)materials may be used. The common denominator of these materials is that they have growth-adaptive behavior. In the end, any biological material/biomaterial could be integrated that shares this feature. However, already extensive in vivo experiences do exist for the following materials:
i) A rapidly (bio-)degradable polymer. Several different fully biodegradable, synthetic polymers exist that could be used as "growth material insert", such as poly-glycolic acid, polycaprolactic acid, or poly-4-hydroxybutyrate. The degradation behavior and biocompatibility of biodegradable (co-)polymer matrices for cardiovascular repair has been extensively investigated in several different in vivo animal models, including ovine and non-human primate models (Weber B., et al. 2011; Schmidt et al., 2010). Also the growth-adaptive capacity of these materials has been investigated and reported. In addition, the in vivo implantation and functionality of PGA-P4HB matrices integrated into metal-based stent (application) systems has been investigated in vivo.
ii) Native biological tissues. Biological native animal or human derived (fixed or decellularized tissues) with expansive capacities different from the transplanted valve tissue, e.g. decellularized enteral mucosa, etc.
iii) or (viable and/or decellularized) tissue engineered materials. Cell-derived or cell-based tissue engineered materials have shown adequate (bio)functional in vivo performance as well as significant growth potential when implanted in preclinical large animal models (Hoerstrup et al., 2006). Importantly, recent studies have focused on the use of decellularized materials as this would allow off-the-shelf use. These in vitro (Dijkman et al., 2012) and in vivo (Weber et al., 2013) studies in preclinical models have revealed substantial recellularization of these human matrices suggesting these materials to be ideal, off-the-shelf materials for cardiovascular regeneration.

Example: Valve Replacement in Pediatric Patients Needing Aortic Valve Repair

In pediatric patients with the necessity for aortic valve repair (e.g. due to congenital aortic valve stenosis) the necessity for repeated reoperation leads to an increased morbidity and mortality. Such patients are expected to benefit from a heart valve replacement as explained herein.

For this purpose, human donor cells (i.e. cells isolated from healthy donor vessels) are used for the in vitro fabrication of a tissue engineered matrix. Briefly, isolated vascular myofibroblastic cells are seeded onto a biodegradable PGA-P4HB-based starter matrix. After static incubation, the construct is placed into a pulsatile dynamic flow bioreactor system for the in vitro generation of a tissue engineered matrix via biomimetic conditioning. Next, the matrix is decelllularized using a standardized protocol (detailed protocol published by Dijkman PE 2012, see references). The human cell-derived decellularized homologous (potentially growth-adaptive) matrix is then integrated into the intercommisural tubular part of a homologous (human cadaver-derived) valve replacement and used for surgical implantation into the orthotopic aortic valve position.

REFERENCES

Schoen F J. Evolving concepts of cardiac valve dynamics: the continuum of development, functional structure, pathobiology, and tissue engineering. Circulation. 2008 Oct. 28; 118(18):1864-80.
Talwar S, Malankar D, Garg S, Choudhary S K, Saxena A, Velayoudham D, Kumar A S. Aortic valve replacement with biological substitutes in children. Asian Cardiovasc Thorac Ann. 2012 October; 20(5):518-24.
Mirensky T L, Nelson G N, Brennan M P, Roh J D, Hibino N, Yi T, Shinoka T, Breuer C K. Tissue-engineered arterial grafts: long-term results after implantation in a small animal model. J Pediatr Surg. 2009 June; 44(6):1127-32;
Hoerstrup S P, Cummings Mrcs I, Lachat M, Schoen F J, Jenni R, Leschka S, Neuenschwander S, Schmidt D, Mol A, Günter C, Gössi M, Genoni M, Zund G. Functional growth in tissue-engineered living, vascular grafts: follow-up at 100 weeks in a large animal model. Circulation. 2006 Jul. 4; 114(1 Suppl):1159-66.
Dolgin E. Taking tissue engineering to heart. Nat Med. 2011; 17(9):1032-5.
Vogel G. Tissue engineering. Mending the youngest hearts. Science. 2011; 333(6046):1088-9.
Hibino N, McGillicuddy E, Matsumura G, Ichihara Y, Naito Y, Breuer C, Shinoka T. Late-term results of tissue-engineered vascular grafts in humans. J Thorac Cardiovasc Surg. 2010 February; 139(2):431-6
Weber B, Scherman J, Emmert M Y, Gruenenfelder J, Verbeek R, Bracher M, et al. Injectable living marrow stromal cell-based autologous tissue engineered heart valves: first experiences with a one-step intervention in primates. Eur Heart J. 2011; 32(22):2830-40.

Schmidt D, Dijkman P E, Driessen-Mol A, Stenger R, Mariani C, Puolakka A, et al. Minimally-invasive implantation of living tissue engineered heart valves: a comprehensive approach from autologous vascular cells to stem cells. J Am Coll Cardiol. 2010; 3; 56(6):510-20.

Dijkman P E, Driessen-Mol A, Frese L, Hoerstrup S P, Baaijens F P. Decellularized homologous tissue-engineered heart valves as off-the-shelf alternatives to xeno- and homografts. Biomaterials. 2012 June; 33(18):4545-54.

Weber B, Dijkman P E, Scherman J, Sanders B, Emmert M Y, Grünenfelder J, Verbeek R, Bracher M, Black M, Franz T, Kortsmit J, Modregger P, Peter S, Stampanoni M, Roberta J, Kehl D, van Doeselaar M, Schweiger M, Brokopp C E, Wälchli T, Falk V, Zilla P, Driessen-Mol A, Baaijens F P T, Hoerstrup S P. Off-the-shelf human decellularized tissue-engineered heart valves in a non-human primate model. Biomaterials 2013.

The invention claimed is:

1. A biological heart valve replacement comprising:
   a tubular segment comprising a proximal end, a distal end, and a central portion arranged between said proximal and distal ends, defining a longitudinal direction of the valve and having an inner wall region, the valve further comprising
   at least one inner leaflet attached, in hinge-like manner, to a connection zone at the inner wall region of said central portion,
   each one of said inner leaflets being movable between a closing position and an opening position of the valve, wherein said tubular segment comprises at least one tubular growth zone in form of a longitudinal strip made of a growth-adaptive biomaterial adapted to increase its size concomitantly with surrounding organ structures of a host, with the remainder of the tubular segment being made of a non-growth-adaptive biomaterial, wherein each inner leaflet further comprises a leaflet growth zone in form of a patch made of said growth-adaptive biomaterial and arranged in a leaflet region adjacent said connection zone.

2. The biological heart valve replacement according to claim 1, having one tubular growth zone for each inner leaflet, each tubular growth zone traversing the connection zone of the respective inner leaflet.

3. The biological heart valve replacement according to claim 1, having two tubular growth zones for each inner leaflet, the two tubular growth zones being circumferentially spaced apart from each other, both growth zones traversing the connection zone of the respective inner leaflet.

4. The biological heart valve replacement according to claim 1, wherein an area formed by an entirety of said tubular growth zones represents 5 to 50 area % of the tubular segment.

5. The biological heart valve replacement according to claim 4, wherein the area formed by the entirety of said tubular growth zones represents 10 to 30 area-% of the tubular segment.

6. The biological heart valve replacement according to claim 1, wherein said leaflet growth zone is substantially triangular, with a triangle base adjacent said inner wall region.

7. The biological heart valve replacement according to claim 1, wherein said leaflet growth zone represents 5 to 50 area-% of the respective inner leaflet.

8. The biological heart valve replacement according to claim 7, wherein said leaflet growth zone represents 10 to 30 area-% of the respective inner leaflet.

9. The biological heart valve replacement according to claim 1, wherein said growth-adaptive biomaterial is a biodegradable polymer.

10. The biological heart valve replacement according to claim 9, wherein said biodegradable polymer is made from a polyglycolic acid matrix dip-coated with poly-4-hydroxybutyrate.

11. The biological heart valve replacement according to claim 1, wherein said tubular segment has a diameter of 5 to 20 mm.

12. The biological heart valve replacement according to claim 1, wherein said tubular segment has a length of 10 to 20 mm.

13. The biological heart valve replacement of claim 1, wherein the heart valve is configured for a pediatric patient.

14. A biological heart valve replacement comprising:
    a tubular segment comprising a proximal end, a distal end, and a central portion arranged between said proximal and distal ends, defining a longitudinal direction of the valve and having an inner wall region, the valve further comprising
    at least one inner leaflet attached, in hinge-like manner, to a connection zone at the inner wall region of said central portion,
    each one of said inner leaflets being movable between a closing position and an opening position of the valve, wherein said tubular segment comprises at least one tubular growth zone in form of a longitudinal strip made of a growth-adaptive biomaterial adapted to increase its size concomitantly with surrounding organ structures of a host, with the remainder of the tubular segment being made of a non-growth-adaptive biomaterial, wherein said non-growth-adaptive biomaterial is a fixed xenogenic tissue or a homogenic native tissue.

15. A biological heart valve replacement comprising:
    a tubular segment comprising a proximal end, a distal end, and a central portion arranged between said proximal and distal ends, defining a longitudinal direction of the valve and having an inner wall region, the valve further comprising
    at least one inner leaflet attached, in hinge-like manner, to a connection zone at the inner wall region of said central portion,
    each one of said inner leaflets being movable between a closing position and an opening position of the valve, wherein said tubular segment comprises at least one tubular growth zone in form of a longitudinal strip made of a growth-adaptive biomaterial adapted to increase its size concomitantly with surrounding organ structures of a host, with the remainder of the tubular segment being made of a non-growth-adaptive biomaterial, wherein said growth-adaptive biomaterial is a tissue engineered material.

16. A method for heart valve replacement comprising:
    implanting a heart valve replacement,
    the heart valve replacement comprising:
    a tubular segment comprising a proximal end, a distal end, and a central portion arranged between said proximal and distal ends, defining a longitudinal direction of the valve and having an inner wall region, the valve further comprising:
    at least one inner leaflet attached in hinge-like manner to a connection zone at the inner wall region of said central portion,
    each one of said inner leaflets being movable between a closing position and an opening position of the valve, wherein said tubular segment comprises at least one tubular growth zone in form of a longitudinal strip made of a growth-adaptive biomaterial adapted to increase its size concomitantly with surrounding organ structures of a host, with the remainder of the tubular segment being made of a non-growth-adaptive biomaterial, wherein each inner leaflet further comprises a leaflet growth zone in form of a patch made of said growth-adaptive biomaterial and arranged in a leaflet region adjacent said connection zone.

* * * * *